US00PP28271P3

(12) United States Plant Patent
Driscoll

(10) Patent No.: US PP28,271 P3
(45) Date of Patent: Aug. 15, 2017

(54) ***CLADRASTIS* TREE NAMED 'WHITE RAIN'**

(50) Latin Name: *Cladrastis kentukea*
Varietal Denomination: White Rain

(71) Applicant: Peter A. Driscoll, Beallsville, MD (US)

(72) Inventor: Peter A. Driscoll, Beallsville, MD (US)

( * ) Notice: Subject to any disclaimer, the term of this patent is extended or adjusted under 35 U.S.C. 154(b) by 1 day.

(21) Appl. No.: 14/756,460

(22) Filed: Sep. 5, 2015

(65) Prior Publication Data

US 2017/0071086 P1 Mar. 9, 2017

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — June Hwu
(74) *Attorney, Agent, or Firm* — C. A. Whealy

(57) ABSTRACT

A new and distinct cultivar of *Cladrastis* tree named 'White Rain', characterized by its outwardly weeping tree form; moderately vigorous to vigorous growth habit; and numerous pendulous inflorescences with white-colored flowers.

2 Drawing Sheets

Botanical designation: *Cladrastis kentukea.*
Cultivar denomination: 'WHITE RAIN'.

BACKGROUND OF THE INVENTION

The present invention relates to a new and distinct cultivar of *Cladrastis* tree, botanically known as *Cladrastis kentukea,* commercially referred to as Yellowwood and hereinafter referred to by the name 'White Rain'.

The new *Cladrastis* tree originated from an open-pollination of an unnamed selection of *Cladrastis kentukea,* not patented, as the female, or seed, parent with an unknown selection of *Cladrastis kentukea* as the male, or pollen, parent. The new *Cladrastis* tree was discovered and selected by the Inventor as a single plant from within the progeny of the stated open-pollination in a controlled environment in Beallsville, Md. during the spring of 2002.

Asexual reproduction of the new *Cladrastis* tree by side veneer grafting in a controlled greenhouse environment in Decherd, Tenn. since February, 2012 has shown that the unique features of this new *Cladrastis* tree are stable and reproduced true to type in successive generations.

SUMMARY OF THE INVENTION

Trees of the new *Cladrastis* have not been observed under all possible combinations of environmental and cultural conditions. The phenotype may vary somewhat with variations in environmental conditions such as temperature and light intensity without, however, any variance in genotype.

The following traits have been repeatedly observed and are determined to be the unique characteristics of 'White Rain'. These characteristics in combination distinguish 'White Rain' as a new and distinct *Cladrastis* tree:

1. Outwardly weeping tree form.
2. Moderately vigorous to vigorous growth habit.
3. Numerous pendulous inflorescences with white-colored flowers.

Trees of the new *Cladrastis* can be compared to trees of the female parent selection. Trees of the new *Cladrastis* differ primarily from trees of the female parent selection in tree form as trees of the female parent selection are upright and not weeping in form.

Trees of the new *Cladrastis* can also be compared to trees of *Cladrastis kentukea* 'Rosea', not patented. Trees of the new *Cladrastis* and 'Rosea' differ primarily in the tree form as trees of the new *Cladrastis* are more weeping and pendulous in habit than trees of 'Rosea'.

BRIEF DESCRIPTION OF THE PHOTOGRAPHS

The accompanying colored photographs illustrate the overall appearance of the new *Cladrastis* tree showing the colors as true as it is reasonably possible to obtain in colored reproductions of this type. Colors in the photographs may differ slightly from the color values cited in the detailed botanical description which accurately describe the colors of the new *Cladrastis* tree.

The photograph on the first sheet is a side perspective view of a typical flowering 13-year old tree of 'White Rain' grown during the spring in an outdoor nursery.

The photograph on the second sheet is a close-up view of a typical flowering tree of 'White Rain'.

DETAILED BOTANICAL DESCRIPTION

The aforementioned photographs and following observations, measurements and values describe trees grown in an outdoor nursery in Decherd, Tenn. and under cultural practices typical of commercial *Cladrastis* tree production. Trees used in the aforementioned photographs and the following description were 13 years old. During the production of the trees, average day temperature was 20° C. and average night temperature was 18° C. In the following description, color references are made to The Royal Horticultural Society Mini Colour Chart, 2007 Edition, except where general terms of ordinary dictionary significance are used.

Botanical classification: *Cladrastis kentukea* 'White Rain'.

Parentage:

*Female, or seed, parent.*—Unnamed selection of *Cladrastis kentukea,* not patented.

*Male, or pollen, parent.*—Unknown selection of *Cladrastis kentukea,* not patented.

Propagation:

*Type.*—By side veneer grafting or budding.

Tree description:

*Tree form and growth habit.*—Deciduous tree with outwardly weeping tree form; freely branching habit with about 15 to 20 lateral branches developing per tree; full and densely-foliated appearance; moderately vigorous to vigorous growth habit.

*Tree height.*—About 2.59 meters.

*Tree width* (*spread*).—About 2 meters.

*Trunk caliper.*—About 62 cm at 150 cm above soil level.

*Growth rate, height.*—About 50 cm to 75 cm per year.

*Growth rate, caliper.*—About 5 cm to 10 cm per year.

*Lateral branch angle orientation* (*angle*).—About 45°.

*Lateral branch length.*—About 75 cm to 100 cm.

*Lateral branch diameter.*—About 2 cm to 3.5 cm.

*Internode length.*—About 6 cm to 9 cm.

*Lateral branch color.*—Close to 144A.

*Immature bark texture.*—Smooth, glabrous.

*Mature bark texture.*—Woody, mostly smooth.

*Mature bark color.*—Close to 194A.

Leaf description:

*Arrangement.*—Alternate, odd-pinnately compound with about seven leaflets per leaf.

*Leaf length.*—About 15 cm to 20 cm.

*Leaf width.*—About 7.5 cm to 11 cm.

*Leaflet length.*—About 4.5 cm.

*Leaflet width.*—About 3 cm.

*Leaflet shape.*—*Ovate.*

*Leaflet apex.*—*Acute.*

*Leaflet base.*—*Obtuse.*

*Leaflet margins.*—Entire.

*Leaflet venation pattern.*—Pinnate.

*Leaflet aspect.*—Pendulous.

*Leaflet texture, upper and lower surfaces.*—Smooth, glabrous.

*Leaflet luster, upper and lower surfaces.*—Matte.

*Leaflet color.*—When developing, upper surface: Close to 137A. When developing, lower surface: Close to 144A. Fully developed, upper surface: Close to 136A; venation, close to 137A. Fully developed, lower surface: Close to 141A; venation, close to 145B. Autumn color, upper surface: Close to 6A. Autumn color, lower surface: Close to 12A.

*Petioles.*—Length: About 5 cm. Diameter: About 2 mm to 2.5 mm. Texture, upper and lower surfaces: Smooth, glabrous. Color, upper and lower surfaces: Close to 137C. Color, lower surface: Close to 144B.

Flower description:

*Flower arrangement and habit.*—Single flowers arranged in pendulous terminal panicled racemes with typically about 20 to 30 flowers developing per inflorescence and about 23 inflorescences developing per tree.

*Fragrance.*—Faintly fragrant; pleasant.

*Natural flowering season.*—Plants of the new *Cladrastis* flower during May until early June in Decherd, Tenn.

*Flower longevity.*—Individual flowers last about eight to eleven days on the plant; flowers not persistent.

*Inflorescence height.*—About 20 cm to 30 cm.

*Inflorescence diameter.*—About 10 cm to 15 cm.

*Flower diameter.*—About 5 mm to 8 mm.

*Flower length* (*depth*).—About 1 cm to 1.5 cm.

*Flower buds.*—Length: About 9 mm to 10 mm. Diameter: About 5 mm to 6 mm. Texture: Smooth, glabrous. Color: Close to N999D.

*Petals.*—Quantity and arrangement: Typically five, fused at the base; upper two lobes fused; lower three lobes free. Length: About 1 cm. Width: About 3 mm to 7 mm. Shape: Upper lobes, roughly orbicular; lower lobes, elongated. Apex: Rounded. Margin: Entire. Texture, upper and lower surfaces: Smooth, glabrous. Luster, upper and lower surfaces: Radiant sheen. Color: When opening, upper and lower surfaces: Close to N999D. Fully opened, upper and lower surfaces: Close to N999D.

*Sepals.*—Calyx length: About 7.5 mm to 10 mm. Calyx diameter: About 5 mm to 6 mm. Quantity and arrangement: Five fused in a campanulate calyx. Length: About 3 mm. Width: About 2 mm. Shape: Lanceolate. Apex: Obtuse. Margin: Entire. Texture, upper and lower surfaces: Smooth, glabrous. Luster, upper and lower surfaces: Matte. Color: When opening, upper and lower surfaces: Close to 149D. Fully opened, upper and lower surfaces: Close to 149D.

*Peduncles.*—Length: About 19 cm to 25 cm. Diameter: About 2 mm. Strength: Strong, flexible. Aspect: Drooping, weeping with weight of flowers. Texture: Smooth, glabrous. Luster: Dull. Color: Close to 138D.

*Pedicels.*—Length: About 1 cm to 1.5 cm. Diameter: About 2 mm. Strength: Strong, flexible. Aspect: Mostly erect. Texture: Smooth, glabrous. Luster: Dull. Color: Close to 138D.

*Reproductive organs.*—Stamens: Quantity per flower: Ten or fewer. Pollen amount: Scarce. Pistils: Pistil length: Less than 1 mm. Stigma color: Close to 2D. Seeds and fruits: Seed and fruit development have not been observed on trees of the new *Cladrastis* to date.

Temperature tolerance: Trees of the new *Cladrastis* have been observed to tolerate high temperatures about 35° C., low temperatures about −11° C. and are suitable for USDA Hardiness Zones 4 through 8.

Pathogen & pest resistance: Trees of the new *Cladrastis* have been not observed to be resistant to pathogens and pests common to *Cladrastis* trees.

It is claimed:

1. A new and distinct *Cladrastis* tree named 'White Rain' as illustrated and described.

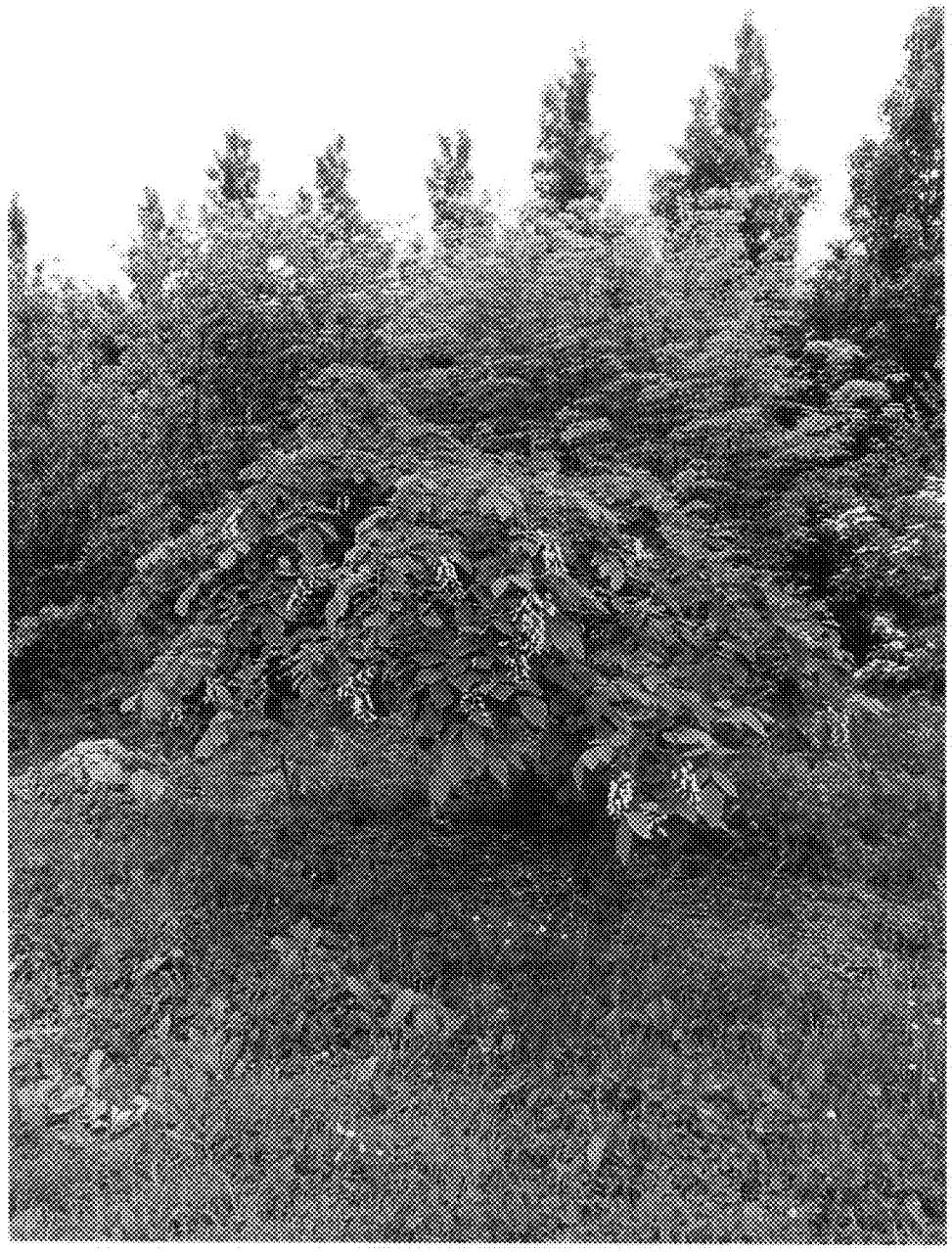

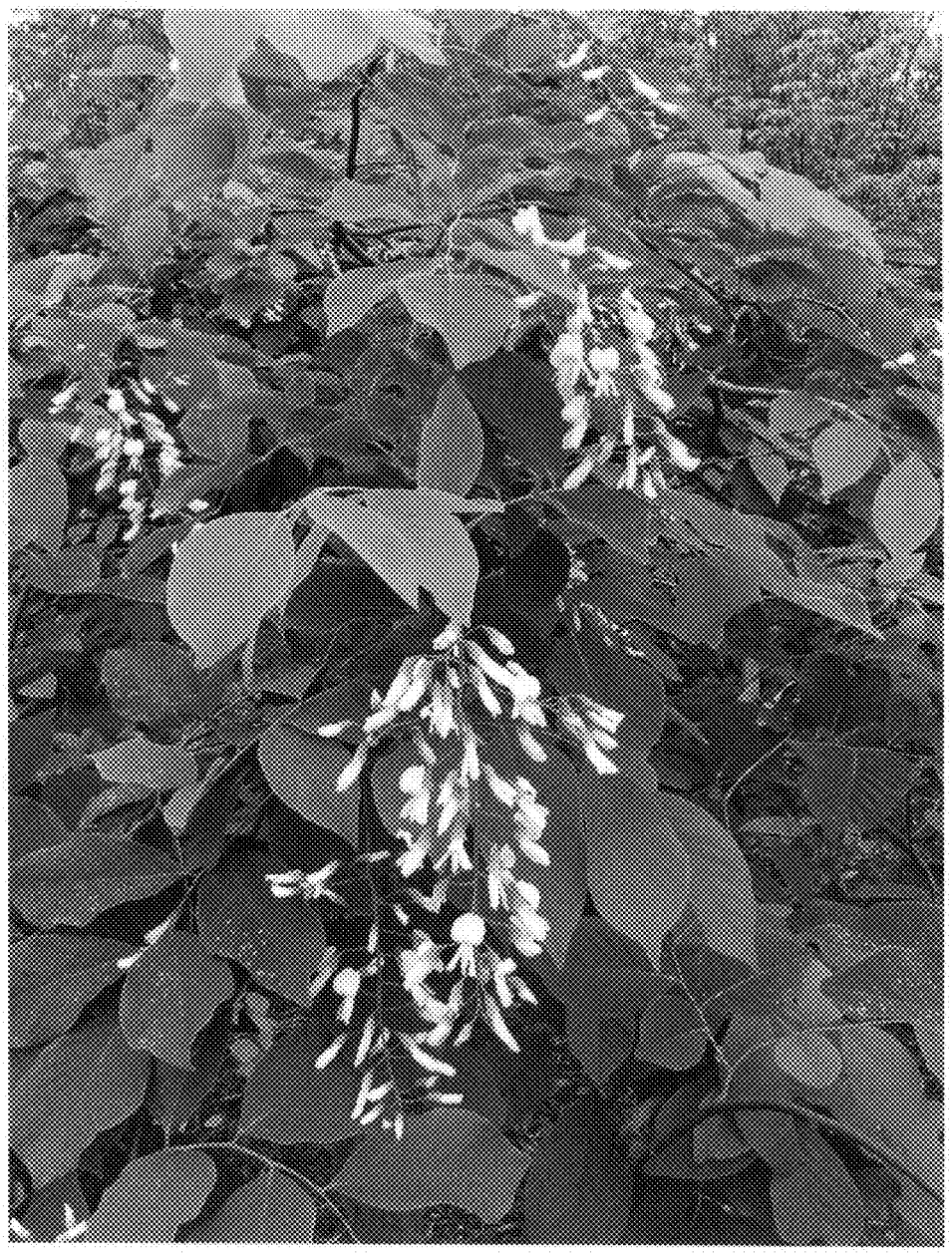

* * * * *